US008574530B2

(12) United States Patent
Formentin et al.

(10) Patent No.: US 8,574,530 B2
(45) Date of Patent: Nov. 5, 2013

(54) PROCESS FOR PRODUCING HYDROCYANIC ACID

(75) Inventors: Enzo Formentin, Noale (IT); Catherine Schafer, Guerting (FR)

(73) Assignee: Arkema France, Colombes (FR)

( * ) Notice: Subject to any disclaimer, the term of this patent is extended or adjusted under 35 U.S.C. 154(b) by 423 days.

(21) Appl. No.: 12/865,873

(22) PCT Filed: Mar. 20, 2009

(86) PCT No.: PCT/FR2009/050472
§ 371 (c)(1),
(2), (4) Date: Oct. 21, 2010

(87) PCT Pub. No.: WO2009/125101
PCT Pub. Date: Oct. 15, 2009

(65) Prior Publication Data
US 2011/0033362 A1 Feb. 10, 2011

(30) Foreign Application Priority Data

Mar. 20, 2008 (FR) ...................................... 08 51807
Jul. 1, 2008 (FR) ...................................... 08 54437

(51) Int. Cl.
*C01C 3/0245* (2006.01)
(52) U.S. Cl.
USPC ........................................................ 423/372
(58) Field of Classification Search
None
See application file for complete search history.

(56) References Cited

U.S. PATENT DOCUMENTS

| 8,039,660 B2* | 10/2011 | Basset et al. ................... 558/338 |
| 2003/0162267 A1* | 8/2003 | Pompejus et al. ............. 435/106 |
| 2003/0233007 A1* | 12/2003 | DeCourcy ...................... 558/371 |
| 2004/0186014 A1* | 9/2004 | Tsukada et al. ............... 502/208 |

FOREIGN PATENT DOCUMENTS

| FR | 1261058 A2 * | 12/1961 |
| WO | WO 2008006977 A1 * | 1/2008 |

OTHER PUBLICATIONS

English translated version of FR 1261058 Dec. 5, 2006.*

* cited by examiner

*Primary Examiner* — Emily Le
*Assistant Examiner* — Jenny Wu
(74) *Attorney, Agent, or Firm* — Smith, Gambrell & Russell, LLP

(57) ABSTRACT

The present invention relates to an improved process for producing hydrocyanic acid by reaction of ammonia with methane in which a small amount of at least one sulphur-containing compound corresponding to the general formula R S $(S)_x$—R' is added, in which R and R', which are identical or different, represent a linear or branched alkyl or alkenyl radical containing from 1 to 5 carbon atoms, and x is a number ranging from 1 to 5, to the reactive gas mixture before it passes over the catalyst. The process according to the invention makes it possible to obtain improved yields of HCN. Another subject of the invention relates to the use of the resulting product for producing methionine, acetone cyanohydrin, adiponitrile or sodium cyanide.

15 Claims, No Drawings

PROCESS FOR PRODUCING HYDROCYANIC ACID

The present invention relates to the manufacture of hydrocyanic acid and one subject thereof is more particularly an improved process for producing hydrocyanic acid by reaction of ammonia over methane in which a sulfur-containing compound belonging to the family of polysulfides, such as dimethyl disulfide, is used.

Hydrocyanic acid HCN has many applications as a reactant in various synthesis routes or as a synthesis intermediate. In particular, it is a key reactant for the preparation of acetone cyanohydrin, synthesis intermediate for the production of methyl methacrylate MMA, base monomer of thermoplastic polymers such as PMMA (Altuglas®, Plexiglas®). Hydrocyanic acid is also used in the synthesis of methionine, or for manufacturing adiponitrile, a synthesis intermediate of polyamide PA-6,6 (Nylon®) and of many chelating agents. Sodium cyanide, a derivative of HCN, also has many applications in the chemical industry.

The current industrial production of hydrocyanic acid HCN is principally based on the Andrussow process dating from the 1930s. This process consists in reacting methane or natural gas over ammonia in the presence of air and optionally oxygen over a catalyst composed of rhodium-plated platinum gauzes. Since the reaction $CH_4+NH_3 \rightarrow HCN+3H_2$ (1) is endothermic, the addition of air makes it possible, by virtue of the combustion of a portion of the hydrogen produced and of the excess of methane, to have a system that is overall exothermic and thus to maintain the synthesis reaction without an external supply of energy.

The reaction, known under the name of ammoxidation, is the following:

$$CH_4+NH_3+3/2O_2 \rightarrow HCN+3H_2O+\text{heat} \qquad (2)$$

The process is based on the reactions (1) and (2).

Due to the extreme sensitivity of the catalyst to poisoning by certain impurities (iron, sulfur, etc.), the quality of the raw materials must be as good as possible. Use is notably made of methane having a purity greater than 90% that contains the minimum of higher hydrocarbons (ethane and especially propane) and that is free of sulfur. The ammonia is filtered and evaporated and preferably does not contain oils or iron. The air has the dust extracted therefrom by washing with water before being compressed.

The three reactants ($CH_4$, $NH_3$, air) are mixed in precise stoichiometric proportions. The resulting gas flow is, after having been filtered, introduced into the reactor. This consists of rhodium-plated platinum gauzes placed on a support and of a quenching furnace that makes it possible to cool the gases immediately after contact with the catalyst. The initiation of the reaction is carried out by virtue of an electric resistance system which ignites the gauzes. Once this ignition has taken place, the overall exothermicity of the reaction maintains the gauzes around 1050-1150° C.

The kinetics are very rapid with a contact time in the vicinity of a few milliseconds or tenths of milliseconds, and a velocity of the gases of around a few meters per second. The proportion of each reactant is optimized so as to obtain a maximum yield and avoid the explosive range of the reaction mixture.

The reaction generally achieves a yield of 60 to 70%, expressed as the number of moles of hydrocyanic acid produced over the number of moles of ammonia introduced, the conversion of the methane being almost quantitative. The hydrocyanic acid selectivity is generally from 80 to 90% (number of moles of HCN produced over the number of moles of $NH_3$ that have reacted).

Another process for producing HCN, the Degussa process, is based on the aforementioned reaction (1), in the absence of oxygen or air, at a temperature of around 1300° C. The reaction then takes place in sintered alumina tubes coated internally with platinum, the bundle of tubes being heated with gas inside a furnace.

In these processes, a portion of the ammonia introduced in order to react over methane, does not participate in HCN being obtained, and either decomposes to nitrogen and hydrogen according to the reaction:

$$2NH_3 \rightarrow N_2+3H_2$$

or remains inert (by-pass).

The first step of purification then consists in neutralizing the unconverted ammonia with sulfuric acid. The solution of ammonium sulfate thus generated is subjected to steam stripping in order to rid it of the traces of HCN still present.

HCN contained in the gases stripped of $NH_3$ is then absorbed in water. At the top of this absorption column predominantly only inert gases and hydrogen remain, which are conveyed to an incinerator. The aqueous solution of HCN is then distilled. HCN exiting at the top is condensed at low temperature. The water exiting at the bottom of this purification column, after having been cooled, is recycled to the absorber. The product obtained at the end of this process has a purity greater than 99% by weight.

These processes, although resulting in a high-purity product, have the drawback of being limited in terms of productivity, since the yields with respect to the ammonia generally only achieve values of around 60-70%.

Various solutions have been researched in order to increase the yield of the reaction of ammonia over methane. In U.S. Pat. No. 3,102,269, it is proposed to add a small amount of a compound containing volatile sulfur during the first hours of the synthesis of HCN in order to reduce the period of activation of the catalyst and increase the selectivity. The preferred compound is carbon disulfide ($CS_2$), but other compounds that contain sulfur may be used, such as thiophene, mercaptans such as methyl, ethyl, propyl or butyl mercaptan, thioethers such as dimethyl sulfide or diethyl sulfide, or hydrogen sulfide. The sulfur-containing compound is added in an amount equivalent to a sulfur content between 2 and 200 mg per $m^3$ of the reaction gas mixture, an amount smaller than 2 mg·S/$m^3$ not giving the desired activation effect and a larger amount, for example 500 mg, becoming a poison for the catalyst. The yield of HCN moved from 61% to 70% with the addition, over 2 hours, of the equivalent of 5 mg of sulfur/$m^3$ gas as $CS_2$.

In the article Journal of Catalysis, 22, (1971), pages 269-279, it is indicated that after a normal production of HCN over a period of around 1000 hours, 100 ppm of $H_2S$ were added over a period of 110 hours. This had the effect of increasing the yield of HCN by 4% and at the same time the temperature of the rhodium-plated platinum gauzes was increased by 20° C.

It is furthermore known that the sulfur which may be present in methane in a significant amount, for example in the form of $SO_2$, $H_2S$, mercaptans or tetrahydrothiophene (odorant agent), is prejudicial to the ammoxidation reaction. Sulfur is also known for modifying the phase diagram of the platinum/rhodium alloy by significantly reducing its melting point and thus modifying the mechanical properties of the catalyst by embrittling it and limiting its service life (Massalski, Binary Alloy Diagrams, ASM International, Materials Park Ohio-1991). According to the article "The Manufacture of Nitric Acid", extract from the journal "Platinum Metals Rev., 1967, 11, (2), 60-69", which is analogous with the HCN process, it is highly recommended to avoid the presence of sulfur-containing compounds in the manufacture of nitric acid, which manufacture uses, just like the HCN process, a reaction between oxygen and ammonia over a rhodium-plated platinum gauze. Such sulfur-containing compounds may, for example, be found in the lubricants of the compressors used for liquefying the ammonia. It is therefore generally recommended to reduce the amount of sulfur-containing compounds in the lubricant to 5 ppm. Likewise the ammonia, if it is from a non-synthetic source, may contain considerable amounts of sulfur, which must first be removed, so that the amount thereof does not exceed 1 or 2 ppm. Furthermore, the air used for the oxidation of the ammonia is generally filtered in order to extract the gaseous impurities of $SO_2$ therefrom.

The role of sulfur in the reaction of ammonia with methane appears complex, beneficial under certain conditions, but also harmful under other conditions. Any data in the literature as regards the nature of the sulfur-containing compounds or the amounts thereof to be used are, furthermore, contradictory.

It has now been discovered, surprisingly, that a sulfur-containing compound belonging to the family of polysulfides, added in small amounts during the production of hydrocyanic acid according to the Andrussow process or the Degussa process significantly increases the yield of HCN with respect to the ammonia. This effect is particularly pronounced when the sulfur-containing compound is a disulfide such as dimethyl disulfide. Even a minimal increase (that is to say from 1 to 5%) in the yield of the HCN manufacturing process has extremely advantageous consequences in terms of gains in productivity. Furthermore, since the activity of the catalysts reduces over time as a function of the usage conditions, the HCN manufacturing yield has a tendency to also decrease over time. The advantage of a solution which makes it possible to increase the yield but also to increase the service life of the catalyst in order to improve the profitability of the production unit is therefore clearly seen.

The effect of dimethyl disulfide on the yield of the reaction has proved substantially greater than that obtained with $H_2S$ customarily used in industrial units.

Dimethyl disulfide of formula $H_3C-S-S-CH_3$, denoted hereinafter by DMDS, or which may also be known as methyl dithiomethane, is used in a large number of applications. In particular, DMDS is used as a sulfiding or pre-sulfiding agent in refineries in order to activate the hydrotreatment catalysts. DMDS is also used in the petrochemical industry for protecting the steam-cracking circuits from the formation of coke and of carbon monoxide. It may also be used as a synthesis intermediate in fine chemistry or in metallurgy for its anti-corrosion properties.

To date, disulfides such as DMDS, or more generally polysulfides, have never been used in a process for producing hydrocyanic acid and the effect thereof is quite unexpected. Without the applicant being tied to any one explanation, the applicant believes that under the operating conditions of the Andrussow process or of the Degussa process, DMDS decomposes into various chemical species which are in equilibrium due to their short residence times in the installation, improving the efficiency of the catalyst, the yield of hydrocyanic acid and reducing the loss of ammonia by decomposition.

One objective of the present invention is therefore to provide a process for producing hydrocyanic acid, having an improved yield, which makes it possible to reduce the loss of ammonia by decomposition and consequently which results in a greater production capacity and/or lower production costs.

One objective of the present invention is also to make possible a shorter activation time of the catalyst and a longer usage time of the catalyst while keeping the same high yield for longer, which makes it possible to improve the profitability of the production unit.

One objective of the present invention is also to provide an improved process for manufacturing hydrocyanic acid which is simple, rapid (comprising as few steps as possible), easy to implement, and which is easily adapted to the existing hydrocyanic acid manufacturing devices in the industry.

One subject of the present invention is a process for producing hydrocyanic acid in which a gas mixture comprising methane (or a natural gas) and ammonia and optionally air and/or oxygen, is passed over a platinum catalyst, characterized in that added to the gas mixture is at least one sulfur-containing compound corresponding to the general formula (I): $R-S-(S)_x-R'$ in which R and R', which are identical or different, represent a linear or branched alkyl or alkenyl radical containing from 1 to 5 carbon atoms and x is a number ranging from 1 to 5.

According to one preferred embodiment of the invention, a gas mixture comprising methane (or a natural gas), ammonia, air and optionally oxygen is passed over a catalyst composed of rhodium-plated platinum gauze.

According to another preferred embodiment of the invention, a gas mixture comprising methane (or a natural gas) and ammonia is passed through sintered alumina tubes coated internally with platinum at a temperature of around 1300° C.

As non-limiting examples of the radicals R and R', mention may be made of the methyl, ethyl, propyl, allyl and propenyl radicals. Preferably, the R or R' radicals are methyl, ethyl or propyl radicals. Among the compounds of formula (I), those for which x ranges from 1 to 3 are preferred, preferably disulfides (x=1) and more particularly dimethyl disulfide (DMDS).

Dimethyl disulfide (DMDS) is a widely available product; it is sold, in particular, by Arkema.

The process according to the invention is characterized in that it comprises the addition of a certain amount of sulfur-containing compound corresponding to the formula (I). The sulfur-containing compound may be added directly to at least one of the raw materials, methane or natural gas, ammonia, or air or oxygen, upstream of the mixing. The sulfur-containing compound may also be added directly to the methane/ammonia or methane/ammonia/air and/or oxygen gas mixture at the mixer or downstream of the mixer in the gas flow before it passes over the catalyst. According to the process of the invention, it is possible to use a single one of these addition possibilities or else to combine several of these various possibilities, the sulfur-containing compound possibly being added via injection at one or more injection points of the process.

The addition of sulfur-containing compound preferably takes place during the normal course of the reaction although it is also possible to add it during the step of activation of the catalyst (24 to 48 hours approximately).

The sulfur-containing compound of formula (I) is preferably added continuously in order to maintain an optimal level of sulfur. The sulfur-containing compound may be added continuously over a period of greater than 30 days of operation of the installation.

The amounts of sulfur-containing compound of formula (I) injected into the gas mixture range from 5 to 500 ppm expressed by a volume of sulfur relative to the volume of methane introduced, preferably from 5 to 200 ppm of sulfur and more particularly from 5 to 100 ppm, and more preferentially still from 5 to 50 ppm expressed by volume of sulfur relative to the volume of methane. These amounts of sulfur-containing compound do not have any damaging impact for the subsequent use of the product obtained from the process according to the invention.

All the other operating parameters of the process may be kept constant, compared to the process without the addition of sulfur-containing compound of formula (I). Typically, in an Andrussow process, use is made of methane having a purity of 95% approximately, the $CH_4/NH_3$ molar ratio ranges from 1.0 to 1.2, the $(CH_4+NH_3)/\text{total}$. $O_2$ molar ratio ranges from 1.5 to 2, preferably from 1.6 to 1.9; the pressure is generally from 1 to 2 bar, the reaction temperature is between 1050° C. and 1150° C.

Under these conditions of parameters that are kept constant (purities of the raw materials, constant molar ratios, constant temperature and pressure, constant residence time, etc.), the effect of the sulfur-containing compound of formula (I) such as DMDS results in an increase in the yield of HCN of 1 to 5% relative to the ammonia introduced, an increase in the selectivity linked to a reduction in the degree of decomposition of the ammonia and an increase in the temperature of the catalyst of 10 to 40° C. Advantageously, the amount of oxygen introduced, where appropriate, may then be reduced, and also the amounts of methane and ammonia, which results in an increase in the productivity.

The process of the invention makes it possible to do away with the use of a toxic gas such as $H_2S$ and calls for a nontoxic liquid product that can easily be vaporized under the conditions of the process (boiling point of around 110° C.). The sulfur-containing compound of formula (I), such as DMDS, makes it possible to significantly improve the productivity of the catalyst used without requiring a supplementary step of purification of the final product. Unlike the use of $H_2S$, the product obtained according to the process of the invention is free of Sulfur-containing compound such as $H_2S$ which enables it to be used directly in any subsequent process in which the presence of sulfur is not desirable, such as a process for preparing acetone cyanohydrin.

Surprisingly, it has furthermore been observed that the sulfur-containing compound of formula (I), such as DMDS, has fewer long-term negative effects on the catalyst, especially from the point of view of the brittleness of the rhodium-plated platinum gauzes or loss of metal, than other sulfur-containing compounds such as $H_2S$ or dimethyl sulfide (DMS). The catalysts can therefore be used over a substantially longer time before being changed.

The invention also relates to the use of at least one sulfur-containing compound corresponding to the general formula (I): R—S—(S)$_x$—R' in which R and R', which are identical or different, represent a linear or branched alkyl or alkenyl radical containing from 1 to 5 carbon atoms and x is a number ranging from 1 to 5, in an effective amount in a process for producing hydrocyanic acid by reaction of ammonia and methane (or natural gas), in order to increase the yield of said process.

The product obtained directly from the process according to the invention is advantageously used for producing methionine or the hydroxy analog of methionine by reaction with methylmercaptopropionaldehyde (MMP).

Methionine, or 2-amino-4-(methylthio)butyric acid, of chemical formula $CH_3—S—(CH_2)_2—CH(NH_2)—COOH$ is an essential amino acid, not synthesized by animals, needed as a supplement in the food intake, especially of poultry, for which the methionine requirements are significant. The methionine obtained by a chemical synthesis route is established as a substitute for supplies of natural origin (fish meal, soybean meal, etc.) for animal feed, mainly for poultry.

Unlike other amino acids, methionine can be assimilated biologically both in the dextrorotatory form (d or +) and in the levorotatory form (l or −), which has enabled the development of chemical syntheses that result in the racemic product. Thus the market for a synthetic methionine is mainly that of dl-methionine, a solid product commonly denoted by DLM. There is also a liquid derivative of methionine, the α-hydroxy acid, corresponding to 2-hydroxy-4-(methylthio)butyric acid of chemical formula $CH_3—S—(CH_2)_2—CH(OH)—COOH$, which has the distinctive feature of being converted in vivo to methionine in a practically quantitative manner. This liquid product, commercially available in the form of an 88 wt % aqueous solution, is commonly denoted by hydroxy analog of methionine.

Numerous syntheses have been described regarding methionine or its hydroxylated derivative, but the chemical processes exploited industrially are essentially based on the same main raw materials and the same key intermediates, namely:

acrolein and methyl mercaptan (MSH) resulting in methylmercaptopropionaldehyde (MMP), also denoted by 3-(methylthio)propanal or by methylthiopropionaldehyde (MTPA);

hydrocyanic acid or sodium cyanide (NaCN), which after reaction with MMP finally results in methionine or in the hydroxy analog of methionine.

Reference may be made to the article: Techniques de l'Ingénieur, traité Génie des Procédés [Treatise on Process Engineering], J 6-410-1 to 9 which describes the industrial processing conditions for processes for the synthesis of methionine using methylmercaptopropionaldehyde and hydrocyanic acid as intermediate products, one of the processes possibly being illustrated schematically by the following reactions:

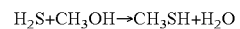

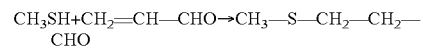

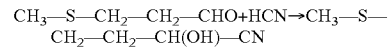

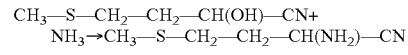

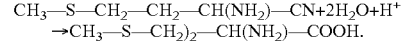

Advantageously, the product obtained directly from the process according to the invention is also used for producing acetone cyanohydrin by reaction with acetone according to the reaction:

Acetone cyanohydrin is an intermediate compound for producing methyl methacrylate (MMA) according to the two routes shown schematically below. A first route consists in forming α-oxyisobutyramide monosulfate, which is converted to methacrylamide sulfate. The latter is then hydrolyzed and esterified with methanol in order to form methyl methacrylate.

A second route consists in reacting directly with methanol, then in using a dehydration reaction in order to result in methyl methacrylate.

Reference may be made to the article: Techniques de l'Ingénieur, traité Génie des Procédés [Treatise on Process Engineering], J 6-400-1 to 6 which describes the industrial processing conditions for the process for producing methyl methacrylate according to the acetone cyanohydrin route.

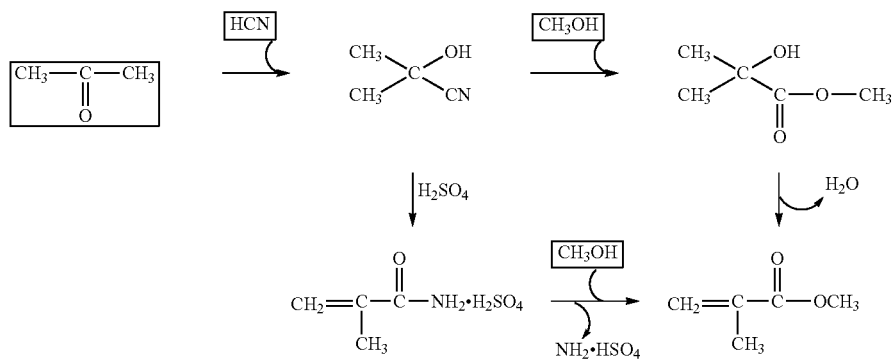

Advantageously, the product obtained directly from the process according to the invention is also used for producing adiponitrile by reaction with butadiene according to the reaction:

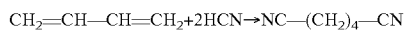

CH$_2$=CH—CH=CH$_2$+2HCN→NC—(CH$_2$)$_4$—CN

Adiponitrile, after hydrogenation, results in hexamethylenediamine which is an intermediate compound for producing polyamide PA-6,6 (Nylon®) by polycondensation of hexamethylenediamine adipate.

Reference may be made to the article: Techniques de l'Ingénieur, traité Génie des Procédés [Treatise on Process Engineering], J 6-515-1 to 7 which describes the synthesis of polyamide PA-6,6 according to this route.

Advantageously, the product obtained directly from the process according to the invention is also used for producing sodium cyanide by neutralization with sodium hydroxide according to the reaction:

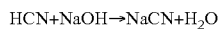

HCN+NaOH→NaCN+H$_2$O

Sodium cyanide has many applications, especially for the extraction of precious metals, electroplating or the synthesis of chemical compounds.

The following examples illustrate the present invention without however limiting the scope thereof.

EXAMPLES

Example 1

Natural gas (NG), without a sulfur-containing compound and with a titer of 95 vol % of methane, is mixed with ammonia, air and oxygen in CH$_4$/NH$_3$ volume proportions of 1.16 and (CH$_4$+NH$_3$)/total O$_2$ volume proportions of 1.70. The flow rate of NG is 4000 kg/h. The mixture is sent through a bed of 15 Pt/Rh (90/10) gauzes. The yield of HCN with respect to ammonia stabilizes at 68.0% after 48 hours, the temperature is then around 1060° C.

DMDS is added in an amount of 10 ppm expressed by volume of sulfur relative to the volume of methane. Very rapidly, the yield increases to 70.0%, the degree of decomposition of the ammonia, determined from the analysis of the N$_2$ and H$_2$ gases at the outlet, drops by 2%, and the temperature of the gauzes increases by +10° C. DMDS is injected continuously which makes it possible to maintain the performances for more than 60 days. Stopping the injection of DMDS gives rise to a gradual drop in the yield. The pure HCN produced does not contain a sulfur-containing compound.

Example 2

The same procedure as example 1 is followed except that DMDS is added in an amount of 125 ppm expressed by volume of sulfur relative to the volume of methane. Very rapidly, the yield increases to 73.0%, the degree of decomposition of the ammonia drops by 4% and the temperature of the gauzes increases by +40° C. DMDS is injected continuously which makes it possible to maintain the performances for more than 50 days. The pure HCN produced does not contain a sulfur-containing compound.

Example 3

Comparative

The same procedure as example 1 is followed except that H$_2$S is added instead of DMDS. H$_2$S is added in an amount of 100 ppm expressed by volume of sulfur relative to the volume of methane. The yield of HCN only increases by 1.0%, the degree of decomposition of the ammonia and the temperature of the gauzes remain practically unchanged. Furthermore, the pure HCN produced contains traces of H$_2$S which are damaging for the downstream application.

Example 4

Natural gas (NG), without a sulfur-containing compound and with a titer of 95 vol % of methane, is mixed with ammonia, air and oxygen in CH$_4$/NH$_3$ volume proportions of 1.16 and (CH$_4$+NH$_3$)/total O$_2$ volume proportions of 1.73. The flow rate of NG is 4100 kg/h. The mixture is sent through a bed of 18 Pt/Rh (90/10) gauzes. The yield of HCN with respect to ammonia is 67% after running for 50 days, the temperature is then around 1060° C.

DMDS is added in an amount of 15 ppm expressed by volume of sulfur relative to the volume of methane. Very rapidly, the yield increases to 69%, the degree of decomposition of the ammonia drops by 3.5% and the temperature of the gauzes increases by +10° C.

Stopping the injection of DMDS gives rise to a drop of the yield to 67%, an increase in the degree of decomposition of the ammonia of 3.5% and a drop in the temperature of 10° C.

DMDS is again injected in an amount of 25 ppm expressed by volume of sulfur relative to the volume of methane. Very rapidly, the yield increases to 69%, the degree of decomposition of the ammonia drops by 3.5% and the temperature of the gauzes increases by 10° C.

Example 5

In a reactor other than that from the preceding examples, natural gas (NG), without a sulfur-containing compound and with a titer of 97 vol % of methane, is mixed with ammonia, air and oxygen in $CH_4/NH_3$ volume proportions of 1.09 and $(CH_4+NH_3)$/total $O_2$ volume proportions of 1.95. The flow rate of NG is 3120 kg/h. The mixture is sent through a bed of 20 Pt/Rh (90/10) gauzes. The yield of HCN with respect to ammonia stabilizes at 64.0% after operating for one week.

DMDS is added in an amount of 10 ppm expressed by volume of sulfur relative to the volume of methane. Very rapidly, the yield increases to 67.0%, the degree of decomposition of the ammonia drops, the temperature of the gauzes increases. DMDS is injected continuously which makes it possible, despite variations in the flow rate of ammonia and of natural gas, to maintain the yield at least 67% for 60 days. A yield of 68% is even obtained by increasing the concentration of DMDS to 20 ppm expressed by volume of sulfur relative to the volume of methane. Stopping the injection of DMDS gives rise to a drop in the yield.

Example 6

Natural gas (NG), without a sulfur-containing compound and with a titer of 94 vol % of methane, doped with DMDS in an amount of 20 ppm expressed by volume of sulfur relative to the volume of methane, is mixed with ammonia, air and oxygen in $CH_4/NH_3$ volume proportions of 1.15 and $(CH_4+NH_3)$/total $O_2$ volume proportions of 1.76. The flow rate of NG is 3840 kg/h. The mixture is sent through a bed of 20 Pt/Rh (90/10) gauzes. The yield of HCN with respect to ammonia is 66.5%, the temperature is then around 1060° C.

Stopping the injection of DMDS gives rise to a drop of the yield to 64%, an increase in the degree of decomposition of the ammonia of 3.5% and a drop in the temperature of 10° C.

$H_2S$ is then added in an amount of 3 ppm expressed by volume of sulfur relative to the volume of methane. The yield of HCN increases by less than 1.0%, the degree of decomposition of the ammonia and the temperature of the gauzes remain practically unchanged.

Stopping the injection of $H_2S$ gives rise to a small drop of the yield to 64%.

The invention claimed is:

1. A process for producing hydrocyanic acid in which a gas mixture comprising methane (or a natural gas) and ammonia and optionally air and/or oxygen, is passed over a platinum catalyst, wherein at least one sulfur-containing compound corresponding to the general formula (I): R—S—(S)$_x$—R' in which R and R', which are identical or different, represent a linear or branched alkyl or alkenyl radical containing from 1 to 5 carbon atoms and x is a number ranging from 1 to 5, is present in the gas mixture.

2. The process as claimed in claim 1, wherein the radicals R and R' are chosen from methyl, ethyl or propyl radicals.

3. The process as claimed in claim 1, wherein the sulfur-containing compound is a disulfide.

4. The process as claimed in claim 1, wherein the sulfur-containing compound is added directly to a component of the gas mixture upstream of the mixing that results in the gas mixture.

5. The process as claimed in claim 1, wherein the sulfur-containing compound is added at the time of the mixing that results in the gas mixture.

6. The process as claimed in claim 1, wherein the sulfur-containing compound is added to the gas mixture before it passes over the catalyst.

7. The process as claimed in claim 1, wherein the amount of sulfur-containing compound added ranges from 5 to 500 ppm expressed by volume of sulfur relative to the volume of methane.

8. The process as claimed in claim 1, wherein the sulfur-containing compound is injected continuously.

9. A method of increasing the yield of hydrocyanic acid which comprises performing the process according to claim 1.

10. A method of producing methionine or the hydroxy analog of methionine which comprises performing the process according to claim 1 and reacting the hydrocyanic acid obtained directly from the process with methylmercaptopropionaldehyde.

11. A method of producing acetone cyanohydrin which comprises performing the process according to claim 1 and reacting the hydrocyanic acid obtained directly from the process with acetone.

12. A method of producing adiponitrile which comprises performing the process according to claim 1 and reacting the hydrocyanic acid obtained directly from the process with butadiene.

13. A method of producing sodium cyanide which comprises performing the process according to claim 1 and neutralizing the hydrocyanic acid obtained directly from the process with sodium hydroxide.

14. The process as claimed in claim 1, wherein the sulfur-containing compound is dimethyl disulfide.

15. The process as claimed in claim 1, wherein the amount of sulfur-containing compound added ranges from 5 to 100 ppm expressed by volume of sulfur relative to the volume of methane.

* * * * *